United States Patent [19]
Whitlock

[11] Patent Number: 5,108,175
[45] Date of Patent: Apr. 28, 1992

[54] LIGHT PHOTON DETECTING APPARATUS

[76] Inventor: Gerald Whitlock, P.O. Box 22, Malvern, Worcestershire WR13 6SL, Great Britain

[21] Appl. No.: 350,612

[22] Filed: May 10, 1989

[30] Foreign Application Priority Data

May 20, 1988 [GB] United Kingdom ................ 8812031

[51] Int. Cl.[5] ............................................ G01N 21/76
[52] U.S. Cl. .................................. 356/218; 250/239; 250/361 C; 422/52; 435/808
[58] Field of Search ................. 250/239, 361 C, 356; 422/52; 435/291, 808; 356/244, 218

[56] References Cited

U.S. PATENT DOCUMENTS

| | | | |
|---|---|---|---|
| 3,940,250 | 2/1976 | Plakas et al. | 250/361 C |
| 3,950,646 | 4/1976 | Whitlock | 250/361 |
| 3,998,592 | 12/1976 | Pyle | 250/361 C |
| 4,841,149 | 6/1989 | Martin et al. | 250/330 |

FOREIGN PATENT DOCUMENTS

| | | |
|---|---|---|
| 1203780 | 9/1970 | United Kingdom . |
| 1403265 | 8/1975 | United Kingdom . |
| 1442237 | 7/1976 | United Kingdom . |
| 1501406 | 2/1978 | United Kingdom . |
| 2056670 | 3/1981 | United Kingdom . |
| 2163553 | 2/1986 | United Kingdom . |
| 2178847 | 2/1987 | United Kingdom . |

Primary Examiner—Vincent P. McGraw
Attorney, Agent, or Firm—Arnold, White & Durkee

[57] ABSTRACT

Light photon detecting apparatus (10) comprises a photomultiplier tube (36) in a two-part housing (14), the underside (22) of which is open. The underside (22) is fitted with an elastomeric sealing ring (28) to make an airtight and hence light-tight seal with a surface (12). Two spring-loaded part (16, 18) of the housing (14) act as a pump to produce a partial vacuum which opens a shutter (60) to expose the photomultiplier tube (36).

15 Claims, 1 Drawing Sheet

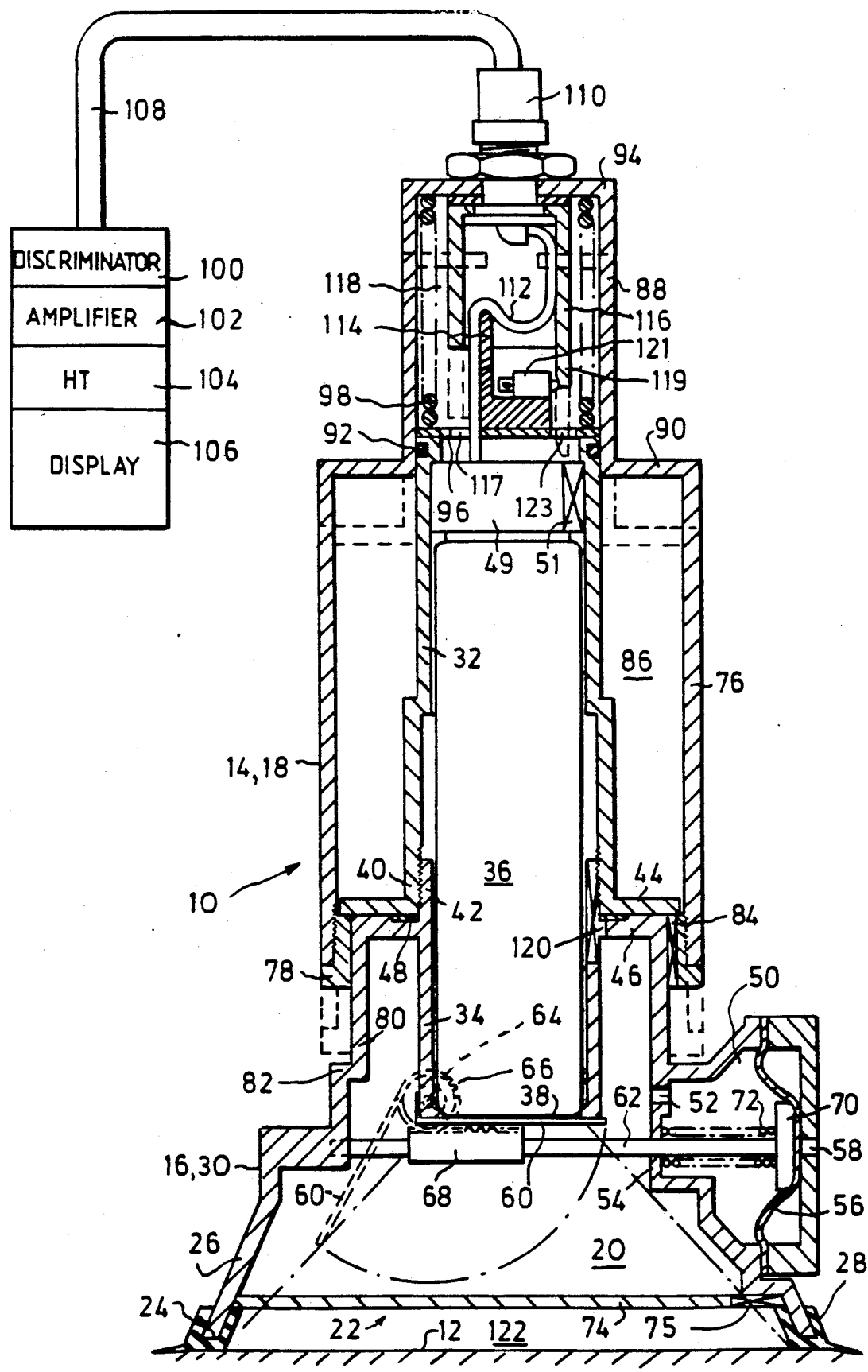

LIGHT PHOTON DETECTING APPARATUS

BACKGROUND OF THE INVENTION

1. Field of the Invention

This invention relates to apparatus for detecting light photons emitted from a surface.

The surface may for example be that of a worktop. The worktop may be suspected of contamination by bacteria and required to be checked for such contamination.

2. Description of the Prior Art

It is know that if bacteria are suitably treated with reagents (such for example as detergent for cell disruption and luciferin-luciferase for reaction with released ATP molecules) light photons are emitted.

SUMMARY OF THE INVENTION

The invention provides apparatus as claimed in each of the claims, to which reference is directed, of this specification. In particular, the apparatus of the invention provides for detecting light photons emitted from a surface, the apparatus comprising a housing defining a chamber whih is optically open at one side defined by a continuous closed edge of a wall of the chamber, a continuous closed elastromeric ceiling member extending completely around the edge to provide a light-tight seal between the chamber and the surface when the edge of the wall is applied with force against the surface, the chamber being light-tight except at its open side, and a photon detector for detecting light photons in the chamber from the surface. The edge lies completely in a single plane for use with a flat surface.

The apparatus of the invention further comprises a means for establishing a pressure differential in the chamber relative to outside the chamber. Additionally, pressure responsive means responsive to loss of or non-establishment of the pressure differential is provided to prevent exposure of the photon detector.

Light responsive means responsive to excess light in the chamber relative to a threshhold prevents overexposure of the photon detector means. Optical means in the chamber close to the open side thereof is adapted for collecting photons from the surface for the photon detector means. A fresnel lens may be used for the optical means.

BRIEF DESCRIPTION OF THE DRAWING

The invention will be described by way of example with reference to the drawing, which is a single figure, partly in section and partly schematic, illustrating apparatus embodying the invention, in combination with other electrical apparatus.

DESCRIPTION OF THE PREFERRED EMBODIMENT

Referring to the drawing,a the illustrated apparatus 10 is adapted for detecting light photons, even single light photons, emitted from a surface 12, which may be the surface of a worktop.

The apparatus 10 comprises a housing 14 which is in two parts, namely, a lower part 16 and an upper part 18.

The lower housing part 16 defines a first chamber 20 which is optically open (that is, transparent) at its underside 22, defined by a continuous closed edge 24 of an outer wall 26, which is of generally annular cross-section, of the chamber 20. A continuous closed elastomeric sealing member 28 extends completely around the wall-edge 24, to provide an hermetic and light-tight seal between the chamber 20 and the surface 12 when the wall-edge 24 is applied with force against the surface 12. The chamber 20 is light-tight except at its optically open underside 22.

The lower housing part 16 is formed of a lower member 30 and an upper member 32. An internal tubular portion 34 of lower member 30 loosely enclosed the lower end portion of a tubular photomultiplier 36, the photon-receptive bottom end 38 of which faces the underside 22 of chamber 20, hence facing the surface 12. The upper member 32 is generally tubular and has an internally screw-threaded bottom end portion 40 screwed tightly onto an externallly screw-threaded, top end, part 42 of internal tubular portion 34 of lower member 30 of lower housing part 16. A bottom end flange 44 of upper member 32 abuts an annular portion 46 of lower member 30, with interposition therebetween of an annular seal 48. The annular portion 46 of lower member 30 extends between the internal tubular portion 34 and the outer wall 26. The upper member 32 encloses, loosely, the upper end portion of the photomultiplier 36, and also encloses a dynode 49, above the photomultiplier 36. The dynode 49 has an air-duct 51 in it.

The lower housing part 16 also comprises a second chamber 50 to one side of the first chamber 20 and communication with the chamber 20 through a first vent 52 in a wall 54 dividing chamber 50 from chamber 20. A completely opaque flexible diaphragm 56 is mounted generally in a vertical plane with the first vent 52 on one side thereof and with a second vent 58, open to atmosphere, on the the other side thereof. Chamber 50 is light-tight on said one side (that of first vent 52) of diaphragm 54 and hence keeps chamber 20 light-tight. The diaphragm 56 is arranged to operate a pivoted shutter 60 in chamber 20 by means of a horizontal shaft 62 which extends slidable through the wall 54. The shutter 60 is pivoted at 64 and carries a toothed pinion 66 meshing with a toothed rack 68 on the shaft 62. A head 70 of shaft 62 is biased away from the wall 54 against the diaphragm 56 by a compression spring 72 on shaft 62, acting between the wall 54 and the shaft-head 70, to pivot the shutter 60 into a horizontal position shutting out light from the photon-receptive bottom end 38 of photomultiplier 36. When a partial vacuum is developed in chamber 20, in a manner described below, the diaphragm 56 is drawn towards the wall 54, moving shaft 62 with it and causing the shutter 60 to pivot open downwardly, by means of rack 68 and pinion 66, to expose the photomultiplier end 38 to the optically-open side 22 of chamber 20.

Beneath the shutter 60, a protective transparent glass plate 74 extends across the open underside 22 of chamber 20, just above the sealing member 28. The plate 74 is supported by the wall 26. The plate 74 may be plane or may form a diffuse light collector, close to the surface 12. It may even take the form of a fresnel lens. It is provided with an air duct 75.

The upper housing part 18 is "telescopically" slidably mounted on the lower housing part 16, to form a pump. More particularly, the upper housing part 18 has a relatively wide lower sleeve portion 76, to the bottom end of which is fixed a ring 78 which fits slidably round a sleeve protion 80 of lower housing part 16. Upward and downward movement of the upper housing part 18 is limited respectively by abutment of the ring 78 against the flange 44 and against an annular step 82 at the bottom end of sleeve protion 80 of lower housing part 16. The ring 78 is provided with a vent 84 which permits airflow to outside atmosphere from a space 86 between sleeve portion 76 of upper housing part 18 and upper member 32 of lower housing part 16, the flange 44 permitting airflow around its edge.

The upper housing part 18 has a relatively narrow upper sleeve portion 88, the bottom end of which is joined integrally to the top end of sleeve portion 76 by a radial wall 90. The upper sleeve portion 88 fits slidable round the upper member 32 of lower housing part 16, with a fluid-tight seal therebetween provided by an elastomeric O-ring 92 seated in an external groove in upper member 32, near the top end of member 32. At the top of the upper sleeve portion 88 is an integral cap 94. A washer 96 rests on the top of the upper member 32 of lower housing part 16. A pre-compressed compression spring 98 is provided, acting between the cap 94 and the washer 96, so that the upper housing part 18 is biased upwardly relative to the lower housing part 16.

Separate from the apparatus 10 are an electrical discriminator 100, electrical amplifier 102, electrical HT (that is, high tension or power) supply 104 and electrical display unit 106, all of a conventional kind for use with a photomultiplier such as the photomultiplier 36, connected to the latter via an electrical cable 108. The cable 108 extends between the discriminator 100 and an electrical terminal 110 mounted on the cap 94. Inside the upper sleeve portion 88 of the upper housing part 18, a flexible electrical cable 112 interconnects the terminal 110 with the photomultiplier 36, via the dynode 49, accommodating the relative movement between the housing parts 16 and 18. A cable guide member 114 is mounted on the top of washer 96 and guides the cable 112 inside a downwardly-open protective shield 116 secured to the cap 94 via the terminal 110. The cable 112 passes through a hole 117 in washer 96, to dynode 49.

The space 118 inside sleeve portion 88 communicates through the duct 51, via a narrow space between the photomultiplier 36 and the inside surface of upper member 32, and through a duct 120 with the chamber 20, which communicates through the duct 75 with the space 122 between surface 12 and plate 74.

In use, the apparatus 10 is placed on the surface 12 and the upper housing part 18 is pressed down against spring 98 to the position shown in dotted lines, reducing the volumes of space 118 and acting as a pump to expel air through duct 51, via the narrow space between photomultiplier 36 and the inside surface of upper member 32, and through ducts 120 and 75, the air escaping under pressure between the sealing member 28 and the surface 12. When upper housing part 18 is released, it rises again due to spring 98, creating a reduction in pressure in chambers 20, 50 and spaces 118 and 122, since sealing member 28 prevents ingress of air.

Each time the upper housing part 18 is pressed down, an extended portion 119 of protective shield 116 actuates a microswitch 121 which permits the high voltage from HT supply 104 to be applied to the photomultiplier 36 via its dynode 49. Loss of vacuum in chambers 20 and 118 causes the upper housing part 18 and with it extended portion 119 of protective shield 116 to rise, due to spring 98, re-setting the microswitch 120 and switching off the high voltage to the photomultiplier 36. This feature safeguards the photomultiplier from being exposed to excessive light on loss of vacuum and failure of pivoted shutter 60 to be operated by diaphragm 56.

The extended portion 119 of shield 116 pokes through a hole 123 in washer 96 when depressed. A circuit may be included which compares the detected light level to a threshold level and switches off power to the photomultiplier if the detected level exceeds the selected threshold level. This circuit also serves to protect the photomultiplier from exposure to excessive light.

The apparatus 10 can "cover" an area of approximately 100 cms$^2$ at a time. To use the apparatus 10 (in conjunction with the other illustrated electrical apparatus) for determining whether a worktop surface is contaminated by bacteria, a proposed mode of use would be to take a "wipe" of a predetermined area—greater (or less) than 100 cms$^2$—of the area by wiping a swab over the surface area, then treating the swab with the reagents mentioned above and then quickly (that is, before the effect of the reagents is exhausted) placing the swab on the surface 12, underneath the apparatus 10, and producing the partial vacuum, as described above, by depressing and then releasing the upper housing part 18. The production of the partial vacuum required close sealing contact between the surface 12 and the sealing member 28 which, as well as keeping out the air, will necessarily also keep out extraneous light at the same time, so the existence of the partial vacuum is an indication that extraneous light is being excluded. The effect of the partial vacuum on the diaphragm 56 causes the shutter 60 to open so that a reading can be taken. If the reading is significant, the worktop area can be checked part-by-part, either directly (if smooth enough and opaque enough) or by the use of further "wipes".

This could be useful in a hospital for example if an outbreak occurs of salmonella food poisoning.

I claim:

1. Apparatus for detecting light photons emitted from a surface, the apparatus comprising a housing, said housing defining a chamber which is optically open at one side of said chamber, said one side being defined by a continuous closed edge of a wall of the chamber, a continuous closed elastomeric sealing member extending completely around the said edge so as to provide a light-tight and hermetic seal between the chamber and the surface when the edge of the wall is applied with force against the surface, the chamber being light-tight except at its open side, photon detector means which is associated with said chamber for detecting individual light photons in the chamber from the surface, means for establishing a pressure differential between the inside and the outside of the chamber when the edge of the wall is applied with force against the surface and the light-tight and hermetic seal is formed between the chamber and the surface, and means responsive to said pressure differential for controlling light exposure of the photon detector means.

2. Apparatus as claimed in claim 1 wherein optical means in the chamber close to the optically open side thereof is adapted for collecting photons from the surface for the photon detector means.

3. Apparatus as claimed in claim 2 wherein the optical means comprises a fresnel lens.

4. Apparatus as claimed in claim 1, wherein said photon detector means comprises a photomultiplier having a photon-receptive end exposed to said chamber.

5. Apparatus as claimed in claim 1, wherein said means for establishing a pressure differential comprises a pump formed by two telescoping portions of said housing.

6. Apparatus as claimed in claim 1, wherein said means responsive to said pressure differential comprises a diaphragm connected to a shutter which is operable for shutting out light from said photon detector means.

7. Apparatus as claimed in claim 1, wherein said means responsive to said pressure differential comprises means for removing electrical power from said photon detector means.

8. Apparatus for detecting light photons emitted from a surface, the apparatus comprising a housing, said housing defining a chamber which is optically open at one side of said chamber, said one side being defined by a continuous closed edge of a wall of the chamber, a continuous closed elastomeric sealing member extending completely around the said edge so as to provide a light-tight and hermetic seal between the chamber and the surface when the edge of the wall is applied with force against the surface, the chamber being light-tight except at its open side, photon detector means which is associated with said chamber for detecting individual light photons in the chamber from the surface, means for establishing a pressure differential between the inside and the outside of the chamber when the edge of the wall is applied with force against the surface and the ligh-tight and hermetic seal is formed between the chamber and the surface, means responsive to said pressure differential for controlling light exposure of the photon detector means, and means responsive to excess light in the chamber for preventing over-exposure to light of the photon detector means.

9. Apparatus as claimed in claim 8 wherein optical means in the chamber close to the optically open side thereof is adapted for collecting photons from the surface for the photon detector means.

10. Apparatus as claimed in claim 9 wherein the optical means comprises a fresnel lens.

11. Apparatus as claimed in claim 8, wherein said photon detector means comprises a photomultiplier having a photon-receptive end exposed to said chamber.

12. Apparatus as claimed in claim 8, wherein said means for establishing a pressure differential comprises a pump formed by two telescoping portions of said housing.

13. Apparatus as claimed in claim 8, wherein said means responsive to said pressure differential comprises an opaque diaphragm connected to a shutter which is operable for shutting out light from said photon detector means.

14. Apparatus as claimed in claim 8, wherein said means responsive to said pressure differential comprises means for removing electrical power from said photon detector means.

15. Apparatus as claimed in claim 8, wherein said means responsive to excess light in the chamber comprises means for removing electrical power from said photon detector means.

* * * * *